United States Patent [19]

Juncosa et al.

[11] Patent Number: 4,729,385

[45] Date of Patent: Mar. 8, 1988

[54] PROBE AND METHOD OF USE FOR DETECTING ABNORMAL TISSUES

[75] Inventors: Robert D. Juncosa, Santa Ana; Richard J. Davies, San Diego, both of Calif.

[73] Assignee: American Mediscan, Inc., Los Angeles, Calif.

[21] Appl. No.: 884,644

[22] Filed: Jul. 11, 1986

Related U.S. Application Data

[62] Division of Ser. No. 790,491, Oct. 23, 1985.

[51] Int. Cl.⁴ .............................................. A61B 5/05
[52] U.S. Cl. ................................................... 128/734
[58] Field of Search ............... 128/637, 639, 642, 733, 128/734

[56] References Cited

U.S. PATENT DOCUMENTS

| | | | |
|---|---|---|---|
| 3,207,151 | 9/1965 | Takagi | 128/734 |
| 3,452,743 | 7/1969 | Rieke | 128/734 |
| 3,971,366 | 7/1976 | Motoyama | 128/734 |
| 4,291,708 | 9/1981 | Forci et al. | 128/734 |
| 4,459,995 | 7/1984 | Conners et al. | 128/734 |

FOREIGN PATENT DOCUMENTS 819742 4/1981 U.S.S.R. .

OTHER PUBLICATIONS

Tedner, "Automatic Recording of Biological Impedances, *Jrnl. Med. Eng. & Tech.*, vol. 2, No. 2, (3/1978).

Primary Examiner—Edward M. Coven
Attorney, Agent, or Firm—George J. Netter

[57] ABSTRACT

Two probes for tissue impedance measurement each have first and second conductive rings unitarily arranged with an insulative member separating the rings. The conductive rings are coaxially arranged and have individual lead wires connected thereto which extend from one end of the probe for connection to external processing and measuring equipment. One probe is of a size enabling insertion within a blood vessel while the other is for location in an epithelial cavity. In use an alternating test signal is applied to the electrodes of each probe and measurements are taken between the two sets of measuring electrodes determining the impedance of the cavity wall tissue lying between the two probes without passing current through the tissue.

2 Claims, 8 Drawing Figures

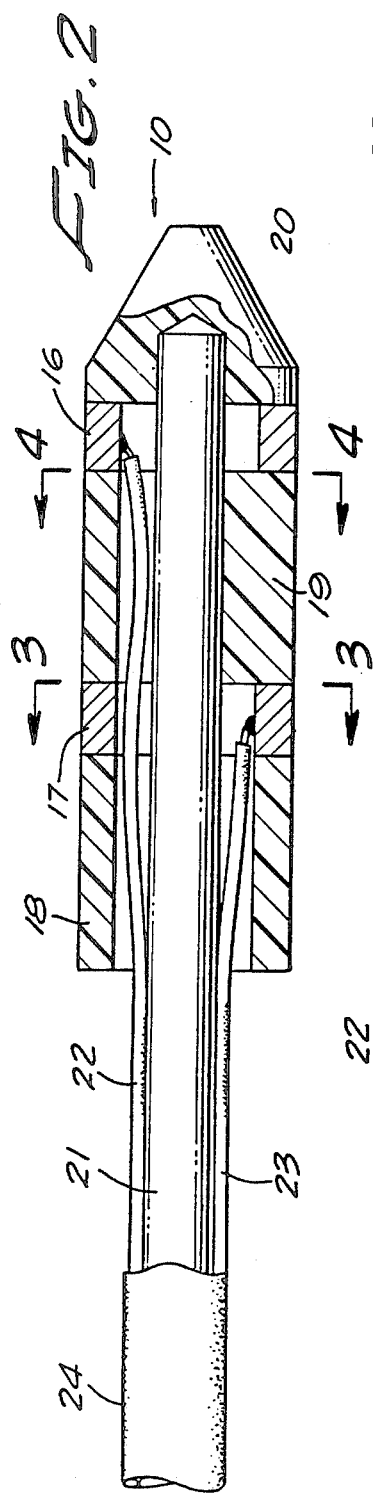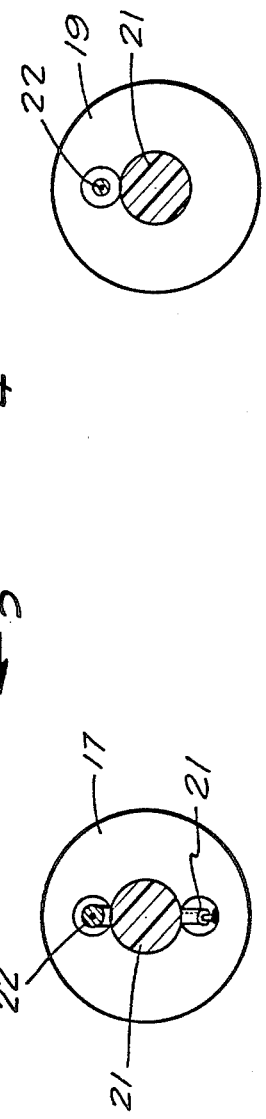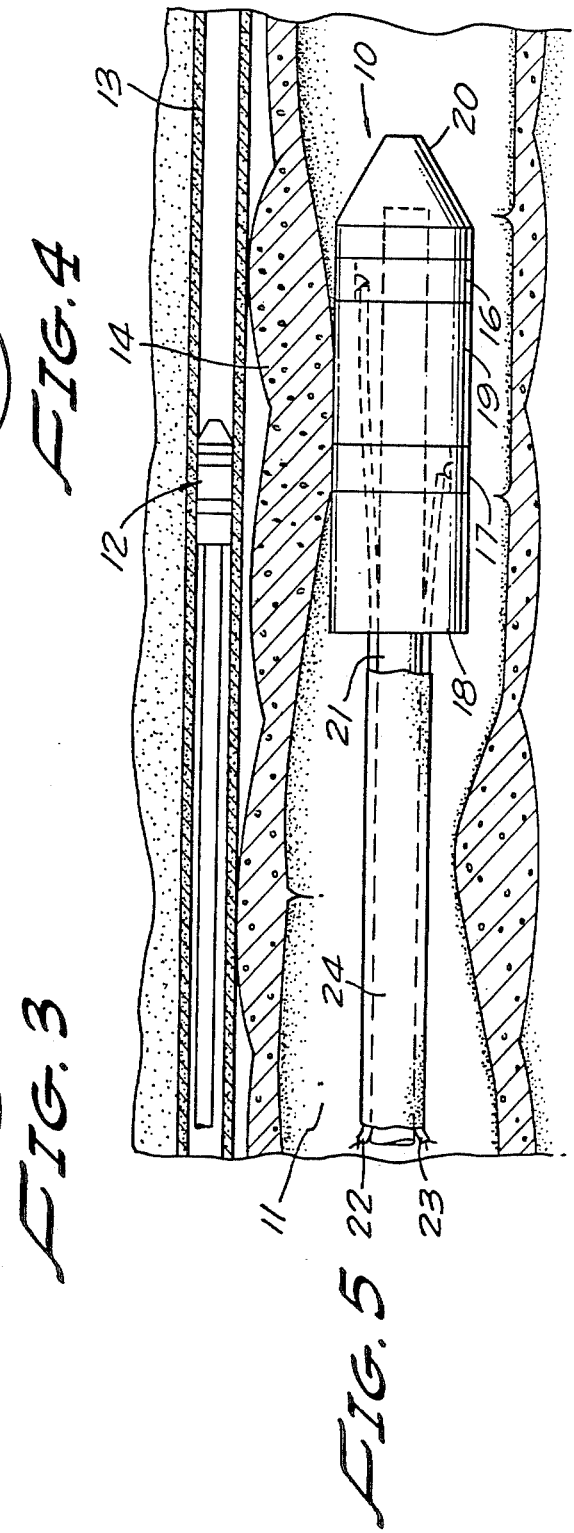

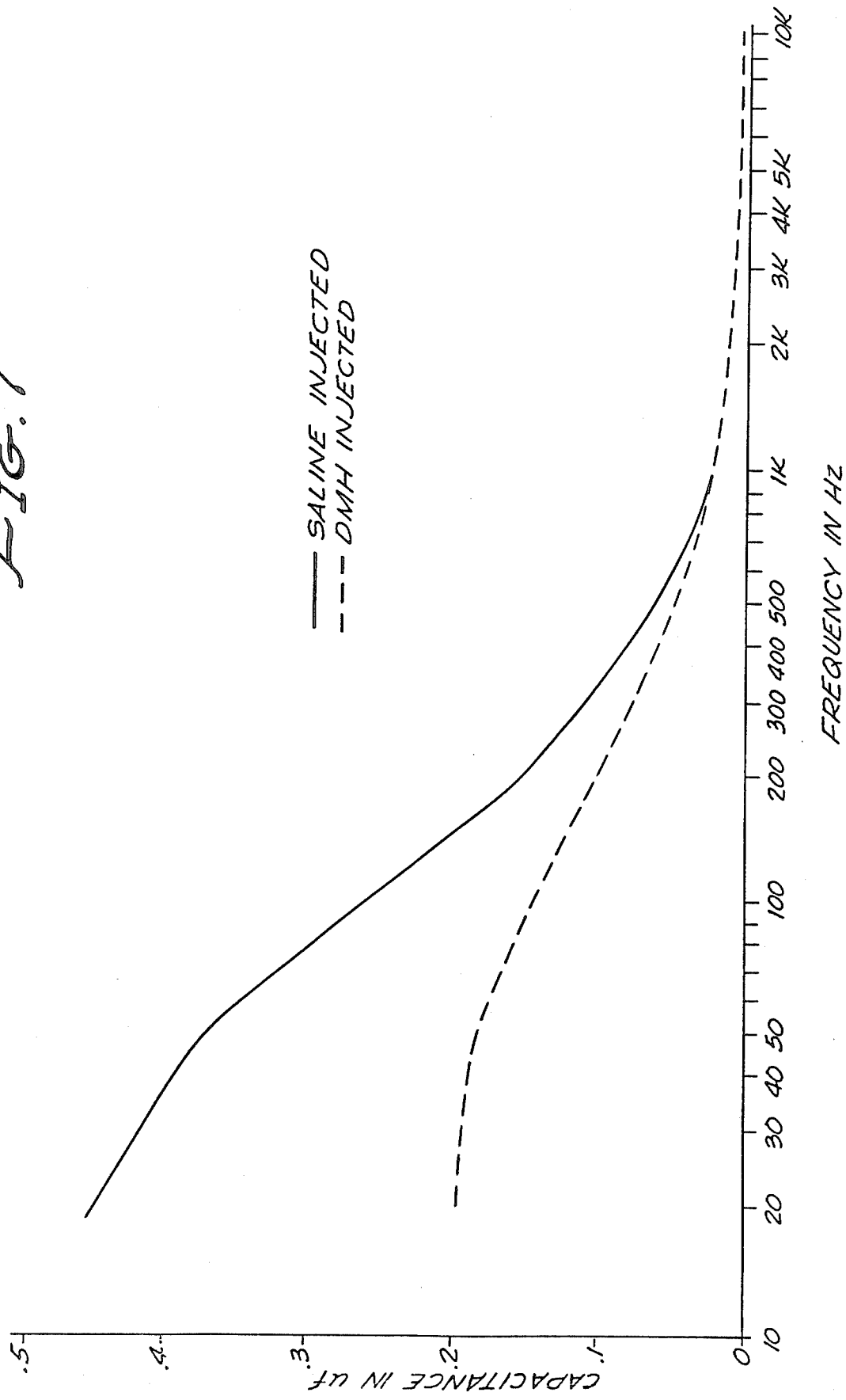

PROBE AND METHOD OF USE FOR DETECTING ABNORMAL TISSUES

This is a division of application Ser. No. 790,491, filed Oct. 23, 1985.

The present invention pertains generally to the detection of the presence of and tendency toward abnormal tissue growth and, more particularly, to a probe and method of use of the probe for the detection of abnormal tissue and an early indication that tested tissue will become abnormal.

BACKGROUND

The term "abnormal tissue" as used herein refers to all forms of tissues which have undergone malignant induction such that these tissues may eventually show loss of growth control which is frequently referred to as cancerous or tumorous growth. The detection of the presence of such abnormal tissues is often made difficult because they are located within the body so that until discomfort or other symptoms are experienced by the individual, the existence of the abnormal tissues may not even be suspected. Additionally, procedures for early detection can be so expensive and complex as to make their use restricted. Therefore, it would be highly advantageous to be able to detect quickly and simply the presence of abnormal tissue or ideally the eventuality of abnormal tissue growth within a body cavity of the host, for example, and preferably the technique should be minimally invasive.

Many forms of cancers or tumors require extended periods of time to achieve a size detectable or injurious to the host, and in some cases this may take many years. Treatment at the present time is considerably more effective when the abnormal tissues are in their early phases and long before they have achieved growth sufficient to cause discomfort or produce symptoms. It would, therefore, also be advantageous to be able to detect the presence of abnormal tissues in their early phases or to detect the tendency for tissues to become abnormal.

Several research efforts have been directed toward discovering the relationship between the electrical impedance of biological tissue and its condition or health. For example, U.S. Pat. No. 3,949,736 discloses that the impedance of biological tissues can provide a useful indication as to whether tissues are healthy or diseased. Specifically, this patent suggests that changes in impedance of biological tissues can be used as a technique for diagnosis of certain carcinomas. According to this patented technique, a low level electric current is passed through the investigated tissue with measurement of the voltage drop across the tissue providing an indirect indication of the overall tissue impedance (i.e., resistance and capacitance). Also, according to this patent, increase in the impedance of the tissue is associated with an abnormal condition of the cells composing the tissue and indicative of a tumor, carcinoma, or other abnormal biological condition of the tissue.

SUMMARY OF THE DISCLOSURE

A probe for use in effecting measurements of tissue impedance consists of first and second conductive rings unitarily arranged with an insulative member separating the rings. The conductive rings, one a measuring and the other a working electrode, are generally coaxially arranged and have individual lead wires connected thereto which extend from one end of the probe for connection to external processing and measuring equipment.

A second probe, which may be constructed in the same manner as the first probe, has electrodes each consisting of annular conductors mounted within an elongated insulative tubular member substantially smaller than the probe, and, in particular, are of a size and shape enabling their receipt within a blood vessel, for example.

In use, the first probe containing one set of electrodes is inserted within an epithelial cavity (e.g., the colon) and located at a test position through the use of an endoscope. Then the second probe is passed along a suitable blood vessel which may be located adjacent to the wall of the tissue defining the epithelial cavity within which the first probe is located. Optionally, the second probe may be located in the skin (either intradermal or subcutaneous), on the skin outer surface, or within a relatively remote blood vessel. An alternating test signal is then applied to the working electrodes of each probe and measurements are taken between the two sets of measuring electrodes determining the impedance of the cavity wall tissue lying between the two probes.

The external measuring and processing system consists of a microcomputer which automatically controls a programmable impedance (resistance and capacitance) for balancing with the measured impedances between the probes, and displaying onto a CRT or other suitable output display device the information obtained. The AC input to the working electrodes is selectable to any desired frequency value over an extensive frequency range (10 Hz–7 KHz).

DESCRIPTION OF THE DRAWING

FIG. 2 is a side elevational, sectional view of an impedance probe of the present invention having two measuring electrodes and interconnecting lead wires.

FIGS. 3 and 4 are end elevational, sectional views taken along the lines 3—3 and 4—4 of FIG. 2, respectively.

FIG. 5 is a side elevational, partially fragmentary view showing the probe and working electrodes in place within the body of the individual.

FIG. 7 is a graph of average tissue impedance measurements taken with the described probe and control and processing equipment.

DESCRIPTION OF A PREFERRED EMBODIMENT

Figure 1:
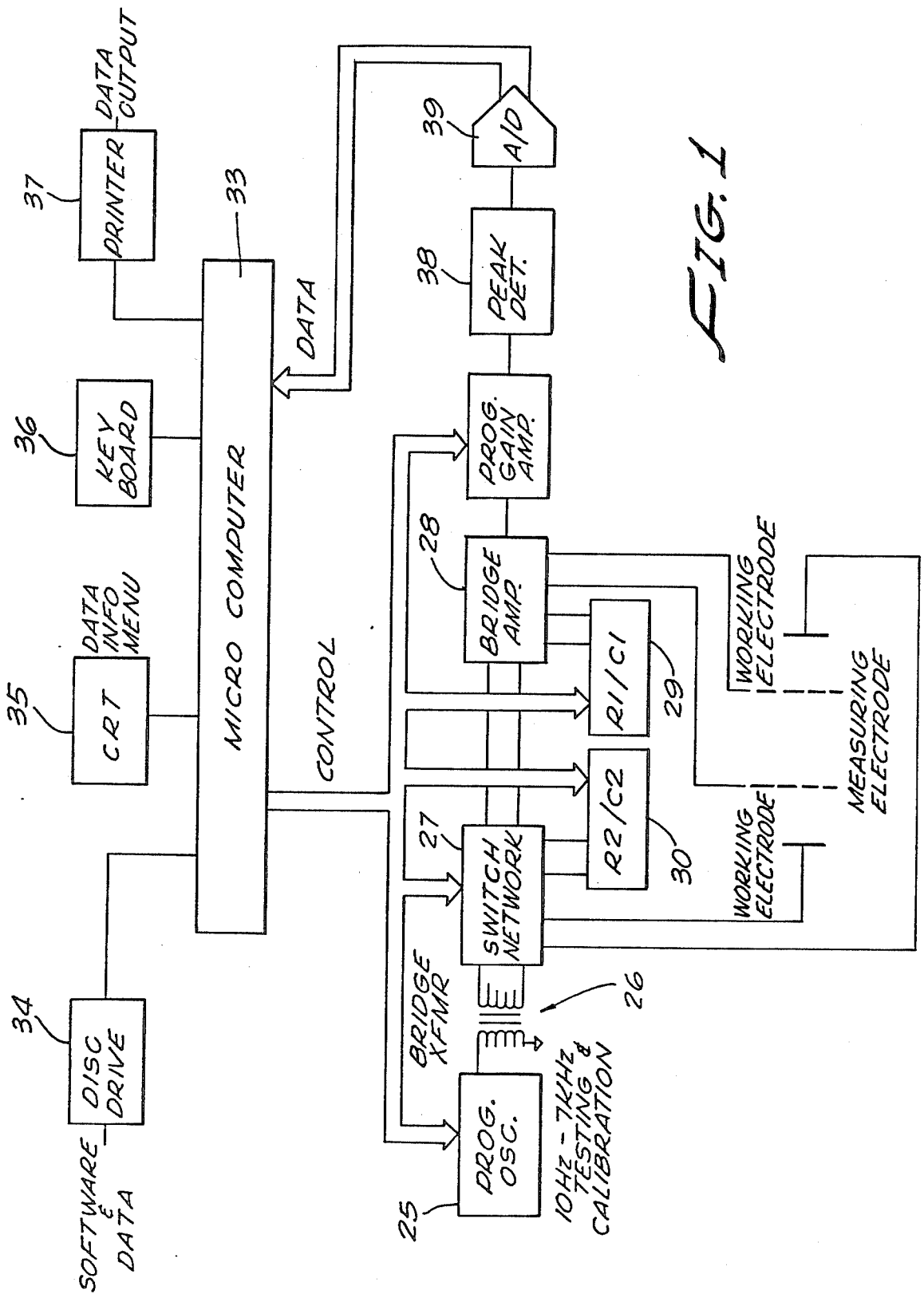
FIG. 1 is a schematic view of the measuring and working electrodes shown interconnected with control and processing equipment.

Turning now to the drawings and particularly FIG. 5, there is shown a probe 10 to be more particularly described which can be readily located within an epithelial cavity 11 of a test subject. The probe 10 in use electrically interacts with a second probe 12 selectively positioned in a blood vessel 13 to measure the impedance of the tissues 14 lying between the two probes.

As has been alluded to generally, and as will be more particularly described later herein, it is a basic premise of the present invention that the magnitude of electrical impedance of the tissues provides a direct indication as to the health or diseased condition of these tissues. It is believed, therefore, that the described techniques will be highly useful in the diagnosis of most epithelial carcinomats such as lung, colon/rectum, cervix, pancreas, bladder, oro-pharynx, naso-pharynx, vagina, urethra, renal calyx, trachea, gall bladder, bile ducts, and small bowel, for example.

As can be seen best in FIG. 2, the probe 10 includes first and second annular metallic electrodes 16 and 17 unitarily assembled with first and second insulative cylinders 18 and 19 and an insulative nose 20. The nose is generally conical and is affixed onto a circular side of the first electrode 16, the opposite side of this electrode being secured to the end wall surface of insulative cylinder 19. Similarly, the second electrode 17 has one side wall affixed to the end wall of cylinder 19 and the other side wall secured to the first insulative cylinder end wall surface.

The electrodes 16 and 17 along with the insulative cylinders 18, 19 and the nose 20 are assembled into a unitary cylindrical affair, the outer surface of which is smooth. A rod-like member 21 extends through the axially arranged bores of the insulative cylinders and electrodes and has its inner end embedded within the nose 20.

A first lead wire 22 extends along the member 21 and has one end conductively secured to an inner part of the electrode 16. A second lead wire 23 extends along the opposite side of member 21 through the bore of cylinder 18 and has its inner end conductively secured to an inner surface of electrode 17. Preferably, the cable wires 22 and 23 are enclosed with the member 21 by a smooth insulative covering 24 to protect surrounding tissues when the probe is being inserted into and removed from the body of a test subject.

Although other materials may be found suitable for constructing a probe 10, best results to date have been obtained by making annular electrodes 16 and 17 from silver which is coated with silver chloride ($AgCl_2$). This coating increases the electrode surface area approximately 10,000 times which reduces a problem sometimes referred to by the term "electrolytic polarization impedance" to be discussed in detail later herein.

The cylinders 18, 19 and the nose 20 are preferably constructed of a molded or machined synthetic plastic which is non-toxic, a good electrical insulator and can be brought to a highly smooth condition. Suitable materials for this purpose are nylon or the plastic sold under the commercial designation Delryn.

The second probe 12 is preferably constructed in the same manner as probe 10 with a pair of highly conductive cylinders separated by insulative members. The probes 10 and 12 are of a size commensurate with their ultimate use location. Thus, if contemplated for intravenous disposal, they are relatively small, whereas if considered for emplacement within, say, the colon, they can be correspondingly larger.

Biological tissue such as tissue 14 consists generally of semisolids and liquids which from the standpoint of their electrical characteristics act as electrolytes. The interface between the electrolyte and an electrode produces a so-called electrode-polarization impedance on the passage of an electric current therethrough, which can be of such magnitude as to impose a serious error in any tissue impedance measurement, and, therefore, compensation or elimination must be provided. The electrode silver chloride coating by increasing the electrode surface area (e.g., approximately 10,000 times) substantially reduces the electrolytic impedance. However, even with this coating the electrolytic impedance problem cannot be satisfactorily solved in 2-electrode measurement of tissue impedance (i.e., measuring the impedance by passing current through tissues lying between two electrodes). One approach to compensating for electrolytic impedance is to adopt a 4-electrode system, and this general scheme is adopted here. For a detailed discussion of theoretical aspects of this general approach reference is made to the article entitled, "An Operational Amplifier 4-Electrode Impedance Bridge for Electrolyte Measurements" by C. D. Ferris and Donald R. Rose in Medical Biological Engineering, Volume 10, pages 647-654, 1972.

For the ensuing discussion of the electrical control and tissue impedance measurement equipment used with the probe 10 and work electrodes 16, 17, reference is now made to FIG. 1. A programmable oscillator 25 is selectively variable to provide test voltage in a range from 10 Hz–7 KHz. The alternating current output of oscillator 25 is applied to a bridge transformer 26 which is interconnected through a switch network 27 and bridge amplifier 28 to apply the selected oscillating voltage signal across certain of the probe electrodes as will be discussed in detail later. In addition, the switch network and bridge amplifier interconnect the electrodes of the two probes 10 and 12 with first and second programmable impedances 29 and 30. Biological tissues do not exhibit electrical inductance characteristics, and, therefore, the programmable impedances are further identified by the schematic representations "R1/C1", "R2/C2".

Figure 6A:
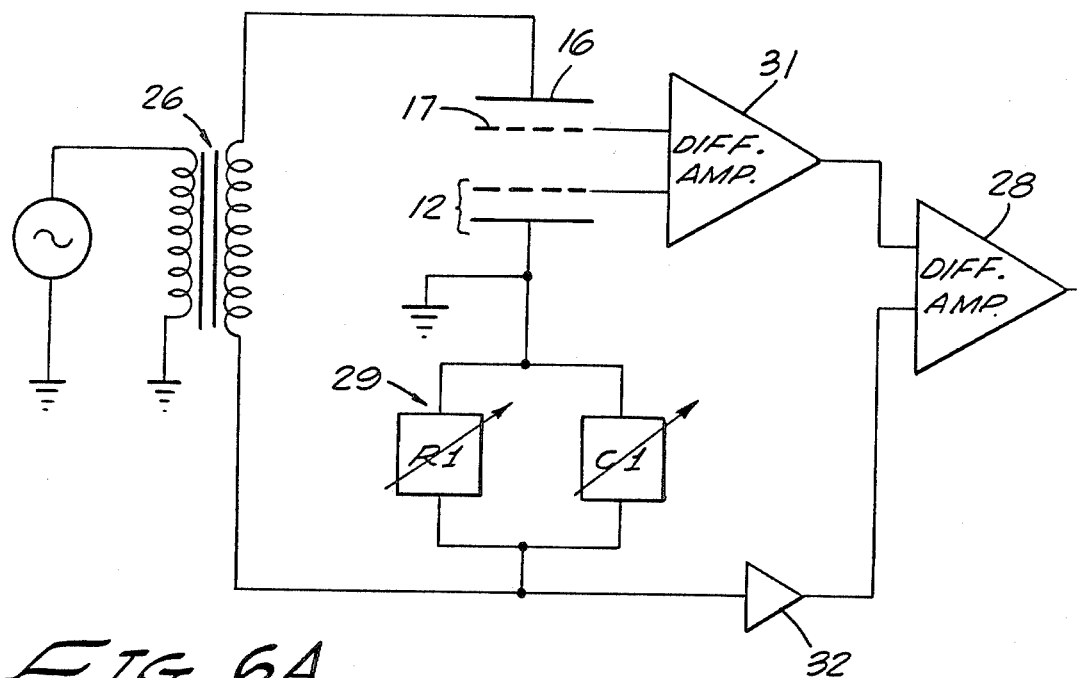
FIGS. 6A and 6B show, respectively, electrical circuit schematics of the two stages for measuring tissue impedance.
Figure 6B:
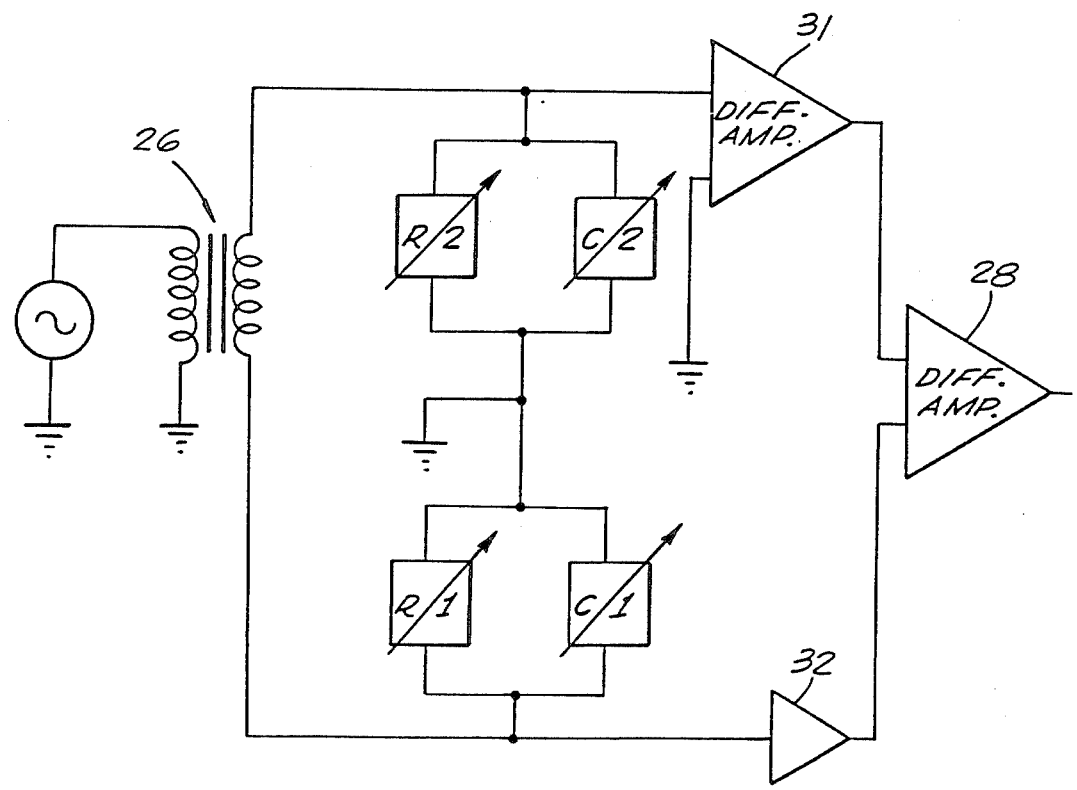

FIGS. 6A and 6B depict, respectively, first and second circuital arrangements used to accomplish what is a two stage tissue impedance measurement. In the first stage circuit, one side of the oscillating voltage signal from the bridge transformer 26 is applied to electrode 17 of probe 10 (which may be termed a "working" electrode) while the electrode 16 (a "measuring" electrode) is fed as one input to a differential amplifier 31. The other terminal of transformer 26 is connected to a common point of the parallel programmable resistance-capacitance arrangement identified as "R1/C1" the other common point of which connects with electrical ground and a working electrode of probe 12. The other, a measuring electrode of probe 12, serves as a second input to differential amplifier 31. The transformer other terminal is fed to a further amplifier 32. The amplification factors of amplifiers 31 and 32 are the same. The signal outputs of amplifiers 31 and 32 feed into bridge amplifier 28, also a differential amplifier.

The first stage measurement provides a first order approximation of the tissue impedance which is the programmed value of "R1/C1" when the bridge circuit is balanced. It is of particular importance to note that in making this measurement virtually no current passes through the tissue 14 and, therefore, the possibility of an error from electrolytic polarization impedances is obviated.

On conclusion of the first stage impedance measurement, the microcomputer 33 (FIG. 1) effects via switch network 27 a substitution of a second set of programmable impedances, R2/C2, for the probes 10 and 12. More particularly, one common point of R2/C2 is connected to the grounded common of R1/C1. The remaining common point of R2/C2 is fed into amplifier 31, the other input being grounded. Adjustment of R2/C2 is then made under control of the microcomputer following which the value of R2/C2 represents a precise measurement of the tissue impedance after the bridge circuit is balanced.

The second stage of balancing "R2/C2" against "R1/C1" acts to neutralize distributed impedances associated with cabling and internal equipment and circuit sources.

Still further as to overall system operation, unbalanced bridge amplifier signals are peak detected at 38, and converted to digital form in the analog-to-digital converter 39 for insertion into the microcomputer. The computer, in turn, automatically adjusts the values of "R1/C1" until the bridge is balanced as indicated by the digital value returned by the A/D converter. Then, in the second stage the adjusted value of R1/C1 is maintained and R2/C2 is adjusted to bridge balance with the final value of R2/C2 being the tissue impedance.

As shown, operation is preferably under the control of a microcomputer 33 which may have a conventional set of peripherals, such as disc drive 34, cathode ray tube display 35 ("CRT"), key board 36, and printer 37. The values of R2/C2 and R1/C1 are automatically changed to achieve the highly accurate two-stage measurement of tissue impedance. A single output frequency of oscillator 25 can be selected by inserting a proper command via keyboard 36, for example, or the computer program can specify another frequency or consecutive set of frequencies desired for impedance measurement. Also, a graphical representation of tissue impedance values measured can be displayed at the CRT 35 and printed out in desired manner at 37.

FIG. 7 is a graph showing a number of impedance traces taken of various test subjects and over an extended frequency range of test voltage. The straight line traces are measurements made of test animal tissues with inbred resistance to abnormal tissue growth not otherwise known to be diseased, and which animals had been given fourteen (14) weekly injections of physiological saline, and, therefore, are concluded to be "healthy" tissues. The dotted line traces, on the other hand show tissue impedance values obtained from test animals which had received 14 weekly injections of DMH (dimethylhydrazine) a known carcinogen, the majority of which animals develop tumors after twenty-six (26) weeks of injections. As the graph clearly shows, the capacitance of healthy tissues is substantially greater than that of tissues which will eventually develop tumors. Measurements of electrical resistance alone at the same intervals have shown no significant change.

The use of DMH in laboratory animals is generally accepted as a model of large bowel cancer similar to spontaneously occuring cancer in man. See in this connection the comments of N. Thurnherr, E. E. Deschner, E H. Stonehill, M. Lipkin, in Cancer Research, Volume 33, page 940 (1973).

The graph of FIG. 7 depicts the average values of ten (10) different test subject measurements (straight line) as compared with traces taken for the same number of test subjects injected with DMH. The results clearly show that healthy tissue has a substantially greater and definable capacitance than that of the tissues which will become abnormal.

A microcomputer 33 used in a practical construction of the invention is a single-board microcomputer manufactured by Apple Computer and accomplished the described functions under control of the following program:

I/O ASSEMBLY SUBROUTINES

```
4100:            22 ;   $4000  16384   MODE
4100:            23 ;
4100:            24 ;   $4001  16385   FREQ
4100:            25 ;
4100:            26 ;   $4002  16386   GAIN RES      10^0
4100:            27 ;   $4003  16387                 10^1
4100:            28 ;   $4004  16388                 10^2
4100:            29 ;   $4005  16389                 10^3
4100:            30 ;
4100:            31 ;   $4006  16390   BRIDGE GAIN
4100:            32 ;
4100:            33 ;   $4007  16391   R1            10^0
4100:            34 ;   $4008  16392                 10^1
4100:            35 ;   $4009  16393                 10^2
4100:            36 ;   $400A  16394                 10^3
4100:            37 ;
4100:            38 ;   $400B  16395   C1            10^-4
4100:            39 ;   $400C  16396                 10^-3
4100:            40 ;   $400D  16397                 10^-2
4100:            41 ;   $400E  16398                 10^-1
4100:            42 ;
4100:            43 ;   $400F  16399   R2            10^0
4100:            44 ;   $4010  16400                 10^1
4100:            45 ;   $4011  16401                 10^2
4100:            46 ;   $4012  16402                 10^3
4100:            47 ;
4100:            48 ;   $4013  16403   C2            10^-4
4100:            49 ;   $4014  16404                 10^-3
4100:            50 ;   $4015  16405                 10^-2
4100:            51 ;   $4016  16406                 10^-1
4100:            52 ;
4100:            53 ;   $4017  16407   BRIDGE VALUE
4100:            54 ;
```

```
4100:                    55 ;   #4018  16408   TEMP MEMORY USAGE
4100:                    56 ;
4100:                    57 ;   - - - - - - - - - - - - - - - - - -
4100:                    58 ;
4100:                    59 ;        PIA INITIALIZATION ROUTINE
4100:                    60 ;
4100:EA                  61 INIT    NOP
4101:A9 30               62         LDA     #$30
4103:8D 01 C3            63         STA     $C301           LOAD CRA-A
4106:8D 03 C3            64         STA     $C303           LOAD CRB-A
4109:8D 05 C3            65         STA     $C305           LOAD CRA-B
410C:8D 07 C3            66         STA     $C307           LOAD CRB-B
410F:A9 FF               67         LDA     #$FF
4111:8D 00 C3            68         STA     $C300           SET DDRA-A AS OUTPUT
4114:8D 04 C3            69         STA     $C304           SET DDRA-B AS OUTPUT
4117:8D 06 C3            70         STA     $C306           SET DDRB-B AS OUTPUT
411A:A9 00               71         LDA     #$00
411C:8D 02 C3            72         STA     $C302           SET DDRB-A AS INPUT
411F:A9 34               73         LDA     #$34
4121:8D 01 C3            74         STA     $C301           SET CA2-A (   RC CLK  ) LOW
4124:8D 03 C3            75         STA     $C303           SET CB2-A (           ) LOW
4127:8D 05 C3            76         STA     $C305           SET CA2-B (OSC/MODE CLK) LOW
412A:8D 07 C3            77         STA     $C307           SET CB2-B (   RG CLK  ) LOW
412D:                    78 ;
412D:                    79 ;             INITIAL VALUE SETTINGS
412D:                    80 ;
412D:A2 FF               81 AGN1    LDX     #$FF
412F:A9 00               82 AGN1    LDA     #$00
4131:9D 00 40            83         STA     $4000,X         CLEAR VARIABLES
4134:CA                  84         DEX
4135:F0 03     413A      85         BEQ     NXT1
4137:4C 2F 41            86         JMP     AGN1
413A:A9 00               87 NXT1    LDA     #$00
413C:8D 00 40            88         STA     $4000           SET CAL MODE
413F:A9 00               89         LDA     #$00
4141:8D 01 40            90         STA     $4001           OSCILLATOR OFF
4144:A9 04               91         LDA     #$04
4146:8D 05 40            92         STA     $4005           SET GAIN RES TO 4K
4149:A9 00               93         LDA     #$00
414B:8D 06 40            94         STA     $4006           SET BRIDGE GAIN TO 1
414E:A9 01               95         LDA     #$01
4150:8D 0A 40            96         STA     $400A           SET R1 TO 1K
4153:A9 01               97         LDA     #$01
4155:8D 0E 40            98         STA     $400E           SET C1 TO .1000 uf
4158:A9 01               99         LDA     #$01
415A:8D 12 40           100         STA     $4012           SET R2 TO 1K
415D:A9 01              101         LDA     #$01
415F:8D 16 40           102         STA     $4016           SET C2 TO .1000 uf
4162:4C 66 41           103         JMP     LOAD
4165:60                 104         RTS
4166:                   105 ;
4166:                   106 ;               I/O ROUTINE
4166:                   107 ;
4166:EA                 108 LOAD    NOP
4167:AD 01 40           109         LDA     $4001           FREQUENCY CODE
416A:0A                 110         ASL     A
416B:0A                 111         ASL     A
416C:18                 112         CLC
416D:6D 01 40           113         ADC     $4001           MODE CODE
4170:8D 04 C3           114         STA     $C304
4173:A9 3C              115         LDA     #$3C
4175:8D 05 C3           116         STA     $C305           SET CA2-B (OSC/MODE CLK) HIGH
4178:A9 34              117         LDA     #$34
417A:8D 05 C3           118         STA     $C305           SET CA2-B (OSC/MODE CLK) LOW
417D:A2 03              119         LDX     #$03
417F:8A                 120 AGN2    TXA
4180:0A                 121         ASL     A
4181:0A                 122         ASL     A
4182:0A                 123         ASL     A
4183:0A                 124         ASL     A
4184:0A                 125         ASL     A
4185:0A                 126         ASL     A
4186:8D 04 C3           127         STA     $C304           GAIN RES ENABLE (RGE X)
4189:AD 06 40           128         LDA     $4006
418C:0A                 129         ASL     A
418D:0A                 130         ASL     A
418E:0A                 131         ASL     A
418F:0A                 132         ASL     A
4190:18                 133         CLC
```

```
4191:7D 02 40    134        ADC   #4002,X
4194:8D 06 C3    135        STA   $C306   GAIN RES DATA (RGD X) & BRIDGE GAIN
4197:A9 3C       136        LDA   #$3C
4199:8D 07 C3    137        STA   $C307   SET CB2-B (RG CLK) HIGH
419C:A9 34       138        LDA   #$34
419E:8D 07 C3    139        STA   $C307   SET CB2-B (RG CLK) LOW
41A1:8A          140        TXA
41A2:F0 04  41A8 141        BEQ   NXT2
41A4:CA          142        DEX
41A5:4C 7F 41    143        JMP   AGN2
41A8:EA          144 NXT2   NOP
41A9:A2 0F       145 LDRC   LDX   #$0F
41AB:8E 18 40    146 AGN3   STX   $4018
41AE:BD 07 40    147        LDA   $4007,X
41B1:0A          148        ASL   A
41B2:0A          149        ASL   A
41B3:0A          150        ASL   A
41B4:0A          151        ASL   A
41B5:18          152        CLC
41B6:6D 18 40    153        ADC   $4018
41B9:8D 00 C3    154        STA   $C300   RC ENABLE (RCE X) & RC DATA (RCD X)
41BC:A9 3C       155        LDA   #$3C
41BE:8D 01 C3    156        STA   $C301   CA2-A (RC CLK) HIGH
41C1:A9 34       157        LDA   #$34
41C3:8D 01 C3    158        STA   $C301   CA2-A (RC CLK) LOW
41C6:8A          159        TXA
41C7:F0 04  41CD 160        BEQ   NXT3
41C9:CA          161        DEX
41CA:4C AB 41    162        JMP   AGN3
41CD:            163  ;
41CD:            164  ;                   READ BRIDGE VALUE
41CD:            165  ;
41CD:EA          166 NXT3   NOP
41CE:AD 02 C3    167 READ   LDA   $C302
41D1:8D 17 40    168        STA   $4017   BRIDGE VALUE
41D4:60          169 END    RTS
```

MANUAL OPERATION SOFTWARE

```
200  REM
201  REM                VARIABLE LIST
202  REM
204  DIM FRQ(12): DIM FRQ$(12): REM          FREQUENCY VALUES
205  FRQ(0) = 0:FRQ$(0) = "OFF"
206  FRQ(1) = 5:FRQ$(1) = "20"
207  FRQ(2) = 6:FRQ$(2) = "50"
208  FRQ(3) = 7:FRQ$(3) = "70"
209  FRQ(4) = 8:FRQ$(4) = "100"
210  FRQ(5) = 9:FRQ$(5) = "200"
211  FRQ(6) = 10:FRQ$(6) = "500"
212  FRQ(7) = 11:FRQ$(7) = "700"
213  FRQ(8) = 12:FRQ$(8) = "1K"
214  FRQ(9) = 13:FRQ$(9) = "2K"
215  FRQ(10) = 14:FRQ$(10) = "5K"
216  FRQ(11) = 15:FRQ$(11) = "7K"
220  DIM MD(3): DIM MD$(3): REM              MODE VALUES
221  MD(1) = 0:MD$(1) = "CAL"
222  MD(2) = 1:MD$(2) = "M1"
223  MD(3) = 2:MD$(3) = "M2"
230  DIM R1$(12): DIM C1$(12): REM           R1&C1 DISPLAY VALUES
231  DIM R2$(12): DIM C2$(12): REM           R2&C2 DISPLAY VALUES
232  FOR N = 1 TO 12
233  R1$(N) = " - ":C1$(N) = " - "
234  R2$(N) = " - ":C2$(N) = " - "
235  NEXT N
240  DIM BAL(12): DIM BAL$(12)
241  FOR N = 1 TO 12
242  BAL(N) =  PEEK (16389) * 1000 +  PEEK (16388) * 100 +  PEEK (16387) *
     10 +  PEEK (16386)
```

```
243  BAL$(N) = STR$ (BAL(N))
244  NEXT N
250  DIM SYS$(10): REM                        SYSTEM MODES
251  SYS$(1) = "MAN"
252  SYS$(2) = "AUTO"
253  SYS$(3) = "BIT"
254  SYS$(4) = "STBY"
255  SYS$(5) = "AGC"
256  SYS$(6) = "BAL"
257  SYS$(7) = "R1"
258  SYS$(8) = "C1"
259  SYS$(9) = "R2"
260  SYS$(10) = "C2"
1000 REM
1001 REM           MENU CHOICES
1002 REM
1004 GOSUB 10000
1006 SYS = 4: GOSUB 11000
1008 VTAB 22: PRINT BELL$;"MANUAL OPERATION ? ";: GET ANS$: PRINT
1010 VTAB 22: PRINT  SPC( 38);""
1012 IF ANS$ = "Y" THEN  GOTO 2000
1014 VTAB 22: PRINT BELL$;"AUTO OPERATION ? ";: GET ANS$: PRINT
1016 VTAB 22: PRINT  SPC( 30);""
1018 IF ANS$ = "Y" THEN  GOTO 4000
1020 GOTO 1008
2000 REM
2001 REM           MANUAL MODE
2002 REM
2004 SYS = 1: GOSUB 11000
2006 VTAB 22: PRINT BELL$;"SET MODE ? ";: GET ANS$: PRINT
2008 VTAB 22: PRINT  SPC( 38);""
2010 IF ANS$ < > "Y" THEN  GOTO 2026
2012 VTAB 22: PRINT BELL$;"1-CAL 2-M1 3-M2  ? ";: GET ANS$: PRINT
2014 VTAB 22: PRINT  SPC( 38);""
2016 IF ANS$ = "1" THEN MD = 0: GOTO 2024
2018 IF ANS$ = "2" THEN MD = 1: GOTO 2024
2020 IF ANS$ = "3" THEN MD = 2: GOTO 2024
2022 GOTO 2012
2024 GOSUB 12000: GOTO 2006
2026 VTAB 22: PRINT BELL$;"SET FREQUENCY ? ";: GET ANS$: PRINT
2028 VTAB 22: PRINT  SPC( 38);""
2030 IF ANS$ < > "Y" THEN  GOTO 2056
2032 VTAB 22: PRINT BELL$;: INPUT "ENTER FREQ. (HZ) OR '0' FOR OFF : ";ANS$
2034 VTAB 22: PRINT  SPC( 38);""
2036 IF ANS$ = "0" THEN FRQ = 0: GOTO 2054
2038 FOR N = 1 TO 7
2040 IF ANS$ = FRQ$(N) THEN FRQ = N: GOTO 2054
2042 NEXT N
2044 IF ANS$ = "1000" THEN FRQ = 8: GOTO 2054
2046 IF ANS$ = "2000" THEN FRQ = 9: GOTO 2054
2048 IF ANS$ = "5000" THEN FRQ = 10: GOTO 2054
2050 IF ANS$ = "7000" THEN FRQ = 11: GOTO 2054
2052 GOTO 2032
2054 GOSUB 12000: GOTO 2026
2056 VTAB 22: PRINT BELL$;"SET BRIDGE GAIN ? ";: GET ANS$: PRINT
2058 VTAB 22: PRINT  SPC( 38);""
2060 IF ANS$ < > "Y" THEN  GOTO 2076
2062 VTAB 22: PRINT BELL$;: INPUT "ENTER GAIN VALUE : ";ANS$
2064 VTAB 22: PRINT  SPC( 38);""
2066 FOR N = 0 TO 7
2068 IF  STR$ (2 ^ N) = ANS$ THEN GN = N: GOTO 2074
2070 NEXT N
2072 GOTO 2062
2074 GOSUB 12000: GOSUB 13026: GOTO 2056
2076 GOSUB 13000
2078 VTAB 22: PRINT BELL$;: INPUT "ENTER BALANCE VALUE (OR '0') : ";ANS$
```

```
2080  VTAB 22: PRINT  SPC( 38);""
2082  IF  VAL (ANS$) = 0 THEN  GOTO 2102
2084  IF 0 <  VAL (ANS$) < 10000 THEN  GOTO 2088
2086  GOTO 2102
2088  FOR N = 16386 TO 16389: POKE N,0: NEXT N
2090  A = 16385 +  LEN (ANS$)
2092  FOR N = 1 TO  LEN (ANS$): POKE A, VAL ( MID$ (ANS$,N,1))
2094  A = A - 1
2096  NEXT N
2098  GOSUB 13000
2100  GOTO 2078
2102  VTAB 22: PRINT BELL$;: INPUT "ENTER R1 VALUE (OR '0') ";ANS$
2104  VTAB 22: PRINT  SPC( 38);""
2106  IF  VAL (ANS$) = 0 THEN  GOTO 2126
2108  IF 0 <  VAL (ANS$) < 10000 THEN  GOTO 2112
2110  GOTO 2102
2112  FOR N = 16391 TO 16394: POKE N,0: NEXT N
2114  A = 16390 +  LEN (ANS$)
2116  FOR N = 1 TO  LEN (ANS$): POKE A, VAL ( MID$ (ANS$,N,1))
2118  A = A - 1
2120  NEXT N
2122  GOSUB 13000
2124  GOTO 2102
2126  VTAB 22: PRINT BELL$;: INPUT "ENTER C1 VALUE (OR '0') ";ANS$
2128  VTAB 22: PRINT  SPC( 38);""
2130  IF  VAL (ANS$) = 0 THEN  GOTO 2150
2132  IF 0 <  VAL (ANS$) < 10000 THEN  GOTO 2136
2134  GOTO 2126
2136  FOR N = 16395 TO 16398: POKE N,0: NEXT N
2138  A = 16394 +  LEN (ANS$)
2140  FOR N = 1 TO  LEN (ANS$): POKE A, VAL ( MID$ (ANS$,N,1))
2142  A = A - 1
2144  NEXT N
2146  GOSUB 13000
2148  GOTO 2126
2150  VTAB 22: PRINT BELL$;: INPUT "ENTER R2 VALUE (OR '0') ";ANS$
2152  VTAB 22: PRINT  SPC( 38);""
2154  IF  VAL (ANS$) = 0 THEN  GOTO 2174
2156  IF 0 <  VAL (ANS$) < 10000 THEN  GOTO 2160
2158  GOTO 2150
2160  FOR N = 16399 TO 16402: POKE N,0: NEXT N
2162  A = 16398 +  LEN (ANS$)
2164  FOR N = 1 TO  LEN (ANS$): POKE A, VAL ( MID$ (ANS$,N,1))
2166  A = A - 1
2168  NEXT N
2170  GOSUB 13000
2172  GOTO 2150
2174  VTAB 22: PRINT BELL$;: INPUT "ENTER C2 VALUE (OR '0') ";ANS$
2176  VTAB 22: PRINT  SPC( 38);""
2178  IF  VAL (ANS$) = 0 THEN  GOTO 2198
2180  IF 0 <  VAL (ANS$) < 10000 THEN  GOTO 2184
2182  GOTO 2174
2184  FOR N = 16403 TO 16406: POKE N,0: NEXT N
2186  A = 16402 +  LEN (ANS$)
2188  FOR N = 1 TO  LEN (ANS$): POKE A, VAL ( MID$ (ANS$,N,1))
2190  A = A - 1
2192  NEXT N
2194  GOSUB 13000
2196  GOTO 2174
2198  GOTO 1006
9999  END
10000 REM
10001 REM              DISPLAY FORMAT
10002 REM
10004 HOME :T$ = "A M E R I C A N   M E D I S C A N"
10006 HTAB 20 -  INT ( LEN (T$) / 2): PRINT T$
10008 PRINT "----------------------------------"
10010 VTAB 3: PRINT  SPC( 38);""
```

```
10012  VTAB 3: INVERSE
10014  PRINT "SYS";
10016  HTAB 10: PRINT "MODE";
10018  HTAB 19: PRINT "FREQ";
10020  HTAB 30: PRINT "GAIN"
10022  NORMAL
10024  PRINT "----------------------------------": PRINT
10026  HTAB 1: PRINT "FREQ";
10028  HTAB 7: PRINT "BAL";
10030  HTAB 14: PRINT "R1";
10032  HTAB 22: PRINT "C1";
10034  HTAB 29: PRINT "R2";
10036  HTAB 37: PRINT "C2"
10038  VTAB 8
10040  FOR N = 1 TO 11
10042  HTAB 4 - LEN (FRQ$(N)): PRINT FRQ$(N)
10044  NEXT N
10046  VTAB 20: PRINT "----------------------------------"
10048  VTAB 21: HTAB 25: PRINT "VALUE : "
10050  RETURN
11000  REM
11001  REM           DISPLAY SYSTEM DATA
11002  REM
11004  VTAB 3: HTAB 5: PRINT SYS$(SYS); SPC( 5 - LEN (SYS$(SYS)));""
11006 MD = PEEK (16384)
11008  VTAB 3: HTAB 15: PRINT MD$(MD + 1); SPC( 1);""
11010 FRQ = PEEK (16385)
11012  FOR N = 0 TO 11
11014  IF FRQ(N) = FRQ THEN FRQ = N: GOTO 11020
11016  NEXT N
11018  GOTO 11022
11020  VTAB 3: HTAB 24: PRINT FRQ$(FRQ); SPC( 6 - LEN (FRQ$(FRQ)));""
11024 GN$ = STR$ (2 ^ ( PEEK (16390)))
11026  VTAB 3: HTAB 35: PRINT GN$; SPC( 4 - LEN (GN$));""
11028  RETURN
12000  REM
12001  REM           SET MODE,FREQ,GAIN
12002  REM
12004  POKE 16384,MD
12006  POKE 16385,FRQ(FRQ)
12008  POKE 16390,GN
12010  CALL 16742
12012  GOSUB 11000
12014  RETURN
13000  REM
13001  REM           BAL,R1,C1,R2,C2,VALUE / FREQ
13002  REM
13003  IF FRQ = 0 THEN RETURN
13004 BAL$(FRQ) = STR$ ( PEEK (16389) * 1000 + PEEK (16388) * 100 + PEEK
       (16387) * 10 + PEEK (16386))
13006 R1$(FRQ) = STR$ ( PEEK (16394) * 1000 + PEEK (16393) * 100 + PEEK
       (16392) * 10 + PEEK (16391))
13008 C1$(FRQ) = "." + STR$ ( PEEK (16398)) + STR$ ( PEEK (16397)) + STR$
       ( PEEK (16396)) + STR$ ( PEEK (16395))
13010 R2$(FRQ) = STR$ ( PEEK (16402) * 1000 + PEEK (16401) * 100 + PEEK
       (16400) * 10 + PEEK (16399))
13012 C2$(FRQ) = "." + STR$ ( PEEK (16406)) + STR$ ( PEEK (16405)) + STR$
       ( PEEK (16404)) + STR$ ( PEEK (16403))
13014  VTAB 7 + FRQ: HTAB 5: PRINT  SPC( 35);"": VTAB 7 + FRQ
13016  HTAB 10 - LEN (BAL$(FRQ)): PRINT BAL$(FRQ);
13018  HTAB 17 - LEN (R1$(FRQ)): PRINT R1$(FRQ);
13020  HTAB 20: PRINT C1$(FRQ);
13022  HTAB 32 - LEN (R2$(FRQ)): PRINT R2$(FRQ);
13024  HTAB 35: PRINT C2$(FRQ)
13026  CALL 16742:VN = 255:VX = 0
13028  FOR N = 1 TO 5
13030 V = PEEK (16407)
13032  IF VX < V THEN VX = V
```

```
13034   IF VN > V THEN VN = V
13036   NEXT N
13038   IF ABS (VX - VN) > 2 THEN GOTO 13026
13040   VL$ = STR$ ( INT ( ABS ((VX + VN) / 2)))
13042   VTAB 21: HTAB 33: PRINT VL$;"  "
13044   RETURN
```

Ninety (90) percent of human cancers are of epithelial origin. Epithelial cells tend to line hollow organs or line the ducts of glandular tissue. Many of these organs are amenable to examination with endoscopes. For example, the bladder is accessible by a cytoscope, lungs by a bronchoscope, stomach by a gastroscope and so on. It is reasonable to expect that impedance studies can be carried out by simple modifications of these instruments placing a probe at the end of the instrument, so that measurements of capacitance can be made in patients at risk for cancer development in the different organs. The described apparatus and technique, therefore, has far reaching implications in the early detection of premalignant changes in many tissues and, as a result, have a major impact on cancer death rates.

The described techniques would be especially valuable in reducing death rates from large bowel cancer. A colonscope or sigmoidoscope modified to carry a probe of this invention can measure the capacitance of the colonic or rectal mucosa in vivo (inside the patient) and make recommendations based on these studies. At the present time, a patient undergoes colectomy (removal of the diseased bowel) based on the presence of dysplasia (abnormal cells) or cancer. These changes often occur late and advanced cancers not amenable to cure may be found at surgery. It is believed that the altered electrical capacitance of the mucosa antecede the histologic changes by many months, or even years making secondary prevention in these patients a real possibility.

What is claimed is:

1. Method of testing selected internal epithelial tissue of a subject to determine biological condition, comprising the steps of:
    locating first and second electrodes of predetermined fixed spaced apart relation within an epithelial cavity of the subject and in contact with the selected tissue;
    locating third and fourth electrodes of predetermined constant spaced apart relation within a blood vessel of the subject closely adjacent the selected tissue;
    establishing an A. C. voltage in the range of 10 Hz to 7 KHz between the first and fourth electrodes; and
    measuring the impedance of the selected tissue located between the second and third electrodes.

2. Method of testing selected internal epithelial tissue as in claim 1, which includes interconnecting the first, second, third and fourth electrodes to measuring apparatus located externally of the subject.

* * * * *